(12) United States Patent
Prather et al.

(10) Patent No.: US 8,852,078 B2
(45) Date of Patent: Oct. 7, 2014

(54) HIGH-THROUGHPUT AND NON-INVASIVE METHOD TO VITRIFY PORCINE EMBRYOS

(75) Inventors: Randall S. Prather, Rocheport, MO (US); Rongfeng Li, Hohhot (CN); Clifton N. Murphy, Columbia, MO (US); Lee Spate, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 706 days.

(21) Appl. No.: 13/061,222

(22) PCT Filed: Aug. 28, 2009

(86) PCT No.: PCT/US2009/055424
§ 371 (c)(1), (2), (4) Date: May 3, 2011

(87) PCT Pub. No.: WO2010/025404
PCT Pub. Date: Mar. 4, 2010

(65) Prior Publication Data
US 2011/0213198 A1    Sep. 1, 2011

Related U.S. Application Data

(60) Provisional application No. 61/190,515, filed on Aug. 29, 2008.

(51) Int. Cl.
*A61B 17/435* (2006.01)
*A61D 19/04* (2006.01)
*A01N 1/02* (2006.01)

(52) U.S. Cl.
CPC .................................. *A01N 1/0221* (2013.01)
USPC ........................................................... 600/34

(58) Field of Classification Search
CPC ....................................... A01N 1/0205–1/0231
USPC ..................... 600/33–35; 800/13, 14, 21–25; 435/1.1–1.3, 325–408
See application file for complete search history.

(56) References Cited

U.S. PATENT DOCUMENTS

| 6,485,959 B1* | 11/2002 | Demetriou et al. ........... 435/243 |
| 6,503,698 B1* | 1/2003 | Dobrinsky et al. ............ 435/1.3 |
| 2002/0045156 A1* | 4/2002 | Toner et al. ........................ 435/2 |
| 2004/0161735 A1* | 8/2004 | Nottle et al. ...................... 435/2 |

FOREIGN PATENT DOCUMENTS

WO    95/05075 A1    2/1995

OTHER PUBLICATIONS

Esaki R et. al. Cryopreservation of porcine embryos derived from in vitro-matrured oocytes. Biology of Reproduction 71, 432-437 (2004).*

(Continued)

*Primary Examiner* — Catherine B Kuhlman
(74) *Attorney, Agent, or Firm* — Senniger Powers LLP

(57) ABSTRACT

The present invention provides a practical, non-invasive, and efficient method for cryopreservation of an in-vitro-produced porcine embryo. The inventive method treats the NP (such as IVF- or NT-derived) embryo at the one-cell or cleavage stage prior to compaction with high osmolality followed by high speed centrifugation. The high osmolality treatment enlarges the periviteline space, and with centrifugation, enables the separation of the lipids from the cytoplasm. The lipid-separated embryos after high osmolality treatment have been successfully cryopreserved and later recovered and transferred to produce live offspring.

20 Claims, 4 Drawing Sheets

(56) References Cited

OTHER PUBLICATIONS

Beebe, L. F. S., et al., "Assisted Hatching Improves Post-Warming In Vitro Viability of Vitrified Porcine Blastocysts," Abstract 85, Reproduction, Fertility and Development, 2004, p. 164, vol. 16.

Beebe, L. F. S., et al., "Piglets Born From Centrifuged and Vitrified Early and Peri-Hatching Blastocysts," Theriogenology, 2002, pp. 2155-2165, vol. 57.

Berthelot, F., et al., "Birth of Piglets After OPS Vitrification and Transfer of Compacted Morula Stage Embryos with Intact Zona Pellucida," Reproduction Nutrition Development, May-Jun. 2001, pp. 267-272, vol. 41, No. 3.

Cameron, R. D. A., et al., "Farrowing Rates and Litter Size Following Transfer of Vitrified Porcine Embryos into a Commercial Swine Herd," Theriogenology, May 2004, pp. 1533-1543, vol. 61, No. 7-8.

Collins, J. L., et al., "Estimates of Mouse Oviductal Fluid Tonicity Based on Osmotic Responses of Embryos," Biology of Reproduction, May 1999, pp. 1188-1193, vol. 60, No. 5.

Dobrinsky, J. R., "Advancements in Cryopreservation of Domestic Animal Embryos," Theriogenology, Jan. 1, 2002, pp. 285-302, vol. 57, No. 1.

Dobrinsky, J. R., et al., "Birth of Piglets After Transfer of Embryos Cryopreserved by Cytoskeletal Stabilization and Vitrification," Biology of Reproduction, Mar. 2000, pp. 564-570, vol. 62, No. 3.

Dobrinsky, J. R., "Cellular Approach to Cryopreservation of Embryos," Theriogenology, 1996, pp. 17-26, vol. 45, No. 6.

Du, Y., et al., "High Overall In Vitro Efficiency of Porcine Handmade Cloning (HMC) Combining Partial Zona Digestion and Oocyte Trisection with Sequential Culture," Cloning and Stem Cells, 2005, pp. 199-205, vol. 7, No. 3.

Du, Y., et al., "Simplified Cryopreservation of Porcine Cloned Blastocysts," Cryobiology, Apr. 2007, pp. 181-187, vol. 54, No. 2.

Esaki, R., et al., "Cryopreservation of Porcine Embryos Derived from In Vitro-Matured Oocytes," Biology of Reproduction, Aug. 2004, pp. 432-437, vol. 71, No. 2.

Hwang, I.-S., et al., "Osmolarity at Early Culture Stage Affects Development and Expression of Apoptosis Related Genes (Bax-alpha and Bcl-xl) in Pre-Implantation Porcine NT Embryos," Molecular Reproduction and Development, Mar. 2008, pp. 464-471, vol. 75, No. 3.

International Search Report and Written Opinion, PCT/US2009/055424, dated Dec. 10, 2009, 10 pages.

Kikuchi, K., et al., "Morphological Features of Lipid Droplet Transition During Porcine Oocyte Fertilisation and Early Embryonic Development to Blastocyst In Vivo and In Vitro," Zygote, Nov. 2002, pp. 355-366, vol. 10, No. 4.

Kragh, P. M. et al., "Efficient In Vitro Production of Porcine Blastocysts by Handmade Cloning with a Combined Electrical and Chemical Activation," Theriogenology, Oct. 15, 2005, pp. 1536-1545, vol. 64, No. 7.

Lai, L., et al., "Production of Alpha-1,3-Galactosyltransferase Knockout Pigs by Nuclear Transfer Cloning," Science, Feb. 8, 2002, pp. 1089-1092, vol. 295, No. 5557.

Li, R., et al., "Cloned Transgenic Swine Via In Vitro Production and Cryopreservation," Biology of Reproduction, Aug. 2006, pp. 226-230, vol. 75, No. 2.

Li, R., et al., "Concentration and Composition of Free Amino Acids and Osmolalities of Porcine Oviductal and Uterine Fluid and Their Effects on Development of Porcine IVF Embryos," Mol. Reprod. Dev., Sep. 2007, pp. 1228-1235, vol. 74, No. 9.

Li, R., et al., "The Preliminary Research on Freezing Viabilities of Bovine In Vitro Fertilized Embryos," Scientia Agricultura Sinica, 2002, pp. 1125-1129, vol. 35, No. 9.

Machaty, Z., et al., "Complete Activation of Porcine Oocytes Induced by the Sulfhydryl Reagent, Thimerosal," Biology of Reproduction, Nov. 1997, pp. 1123-1127, vol. 57, No. 5.

Misumi, K., et al., "Successful Production of Piglets Derived from Vitrified Morulae and Early Blastocysts Using a Microdroplet Method," Theriogenology, Jul. 2003, pp. 253-260, vol. 60, No. 2.

Nagashima, H., et al., "Changes in Freezing Tolerance of Pig Blastocysts in Peri-Hatching Stage," Jpn. J. Anim. Reprod., Sep. 1989, pp. 130-134, vol. 35, No. 3.

Nagashima, H., et al., "Freezability of Porcine Blastocysts at Different Peri-Hatching Stages," Theriogenology, Apr. 1992, pp. 839-850, vol. 37, No. 4.

Nagashima, H., et al., "Production of Live Piglets Following Cryopreservation of Embryos Derived from In Vitro-Matured Oocytes," Biology of Reproduction, May 2007, pp. 900-905, vol. 76, No. 5.

Nagashima, H., et al., "Removal of Cytoplasmic Lipid Enhances the Tolerance of Porcine Embryos to Chilling," Biology of Reproduction, Oct. 1994, pp. 618-622, vol. 51, No. 4.

Nagashima, H., et al., "Survival of Porcine Delipated Oocytes and Embryos After Cryopreservation by Freezing or Vitrification," Journal of Reproduction and Development, 1999, pp. 167-176, vol. 45, No. 2.

Niemann, H., et al., "Advances in Biotechnology: New Tools in Future Pig Production for Agriculture and Biomedicine," Reprodroduction in Domestic Animals, Apr. 2003, pp. 82-89, vol. 38, No. 2.

Norberg, H. S., "Ultrastructural Aspects of the Preattached Pig Embryo: Cleavage and Early Blastocyst Stages," Z. Anat. Entwickl-lungsgesch., Dec. 31, 1973, pp. 95-114, vol. 143, No. 1.

Polge, C., et al., "The Low Temperature Preservation of Cow, Sheep and Pig Embryos," Cryobiology, 1977, p. 560, vol. 11.

Prather, R. S., et al., "Transgenic Swine for Biomedicine and Agriculture," Theriogenology, Jan. 1, 2003, pp. 115-123, vol. 59, No. 1.

Tao, T., et al., "Development of Pig Embryos Reconstructed by Microinjection of Cultured Fetal Fibroblast Cells into In Vitro Matured Oocytes," Animal Reproduction Science, Jun. 28, 1999, pp. 133-141, vol. 56, No. 2.

Wilmut, I., "The Low Temperature Preservation of Mammalian Embryos," Journal of Reproduction and Fertility, Dec. 1972, pp. 513-514, vol. 31, No. 3.

Cameron, R. D., et al., "Cryopreservation and Transfer of Pig Embryos," Society of Reproduction and Fertility Supplement, 2006, pp. 277-291, vol. 62.

Men, H., et al., "Improved Survival of Vitrified Porcine Embryos After Partial Delipation Through Chemically Stimulated Lipolysis and Inhibition of Apoptosis," Theriogenology, 2006, pp. 2008-2016, vol. 66, No. 8.

\* cited by examiner

HIGH-THROUGHPUT AND NON-INVASIVE METHOD TO VITRIFY PORCINE EMBRYOS

GRANT STATEMENT

The invention was made in part from government support under Grant No. R01 RR013438 and Grant No. U42 RR018877 from the National Institutes of Health. The Government has certain rights in the invention.

FIELD OF INVENTION

The present invention relates to a method of porcine embryo preservation, more particularly to a new and improved method to preserve in-vitro produced porcine embryos.

BACKGROUND OF INVENTION

Successful cryopreservation of early mammalian embryos provides opportunities for the preservation of germplasm as well as the movement of genetics nationally and internationally. Unfortunately, the pig embryo has been more difficult than many mammalian embryos to cryopreserve. Significant advances have been made towards the successful cryopreservation of pig embryos based on the observation that pig embryos are very sensitive to hypothermic conditions and that removal of intracellular lipids (delipation) appears to alleviate this sensitivity [1-4]. Most studies have focused on in vivo produced embryos, as they are considered to be more developmentally competent than in vitro produced embryos. Alternatives to mechanical delipation include destabilizing the cytoskeleton [5] or altering the vitrification conditions [6-8].

According to prior studies on cryopreservation of in vivo produced embryos, after centrifugation of the pig oocyte or embryo with an intact zona pellucida, the polarized lipid droplets tend to remain connected with the cytoplasm of the oocyte or blastomere of the embryo via a bridge-like structure [11]. The polarized lipid droplets can redistribute back into the oocyte or blastomere during subsequent culture or cryopreservation procedures. If the perivitelline space is enlarged, the bridge-like structure will break after centrifugation and the lipid droplets will not redistribute into the cytoplasm of the oocyte or the blastomere of the embryo, but will stay within the intact zona pellucida. Thus in vivo-derived embryos need to be cryopreserved immediately after centrifugation in order to prevent lipid redistribution prior to cryopreservation [12].

Prior studies also found that the lipid droplets are abundant and large in the early stage porcine embryo and gradually decline in size and abundance as the embryo advances to and beyond the blastocyst stage [15, 16]. Interestingly, the large lipid droplets in the early stage embryos are easier to remove by centrifugation than the smaller droplets in the later stage embryos.

In-vitro production of pig embryos, such as embryos derived from in-vitro fertilization (IVF) or by nuclear transfer (NT), has been used to create disease models or potential organ donors for xenotransplantation. As a result, the demand for effective cryopreservation of in vitro produced embryos has dramatically increased. However, in-vitro produced (IVP) embryos are even more sensitive to cryopreservation, thus more difficult to cryopreserve, than their in vivo produced counterparts [9].

So far, very limited success has been achieved to cryopreserve IVP embryos. In 2006, the inventors' lab reported two litters of transgenic piglets produced from cryopreserved NT embryos [9]. Subsequently, Nagashima et al. [10] reported piglets produced from cryopreserved IVF-derived embryos. However both of these successful reports of the cryopreservation of IVF- or NT-derived embryos used mechanical delipation through centrifugation and micromanipulation [9, 10]. Mechanical delipation substantially increases the potential of pathogen transmission because of the damage inflicted upon the zona pellucida during micromanipulation. It is also labor-intensive and time-consuming Two other groups [13, 14] have reported the attempts to employ partial enzymatic digestion and subsequent centrifugation to improve the cryopreservation survival of pig parthenogenetic embryos and hand-made cloned embryos. Specifically, when the zona pellucida is partially digested by trypsin, pronase, or another enzyme, it swells in size, which results in an increase in the amount of space between the oocyte plasma membrane and the zona pellucida. Thus when the oocyte or embryo is centrifuged sufficient space is present for the lipids to completely separate. However, the partial enzymatic digestion treatment has some disadvantages when used for lipid separation. For example, the enzyme (such as Trypsin or Pronase) can elicit parthenogenetic activation of oocytes. Additionally, the enzymatic digestion treatment may not work consistently and needs to be observed and monitored closely in small groups, since the effect of the enzyme treatment is heavily dependent on the individual batch of enzyme. Furthermore, neither group reported any piglet produced from the cryopreserved embryos using the combination of enzymatic digestion and centrifugation method.

Therefore, there is a need to develop a practical and non-invasive method for lipid separation and cryopreservation of IVP (such as IVF-derived or NT-derived) porcine embryos, which is suitable for research and commercial purposes.

SUMMARY OF INVENTION

In one aspect of the invention, a new and improved method to separate or remove the lipids from the cytoplasm of the in-vitro-produced (IVP) (in-vitro-fertilization (IVF) derived or nuclear transfer (NT) produced) porcine embryo is described. The inventive lipid removal method comprises the steps of (1) producing IVP porcine embryos at the one-cell or cleavage stage (prior to compaction), (2) condensing the embryos to produce condensed embryos, and (3) centrifuging the condensed embryos to separate the lipids from the cytoplasm to produce lipid-separated embryos.

According to one embodiment of the inventive method, the volume of embryos may be condensed through high osmolality treatment. Particularly, the IVF- or NT-derived embryos at the one-cell or cleavage stage prior to compaction may be exposed to a medium with a pre-selected osmolality greater than the previous culture medium for a pre-determined short time period. The osmolality of a medium may be adjusted by addition of salt, such as NaCl, sugar, such as Sucrose, raffinose, fructose, mannitol ortrehalose, or other organic reagents, such as DMSO, or ethylene glycol, to the medium according to any standard procedure.

In another aspect of the invention, a new and improved method for cryopreservation and later transfer of the lipid-separated IVF- or NT-derived porcine embryos is described. The lipid-separated porcine embryos may be cryopreserved after further embryo development to the blastocyst stage and subjecting such to vitrification. The vitrified embryos may be warmed, have their zonae pellucidae removed, and transferred into a recipient (such as a surrogate pig).

DETAILED DESCRIPTION OF INVENTION

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

The present invention, building on the prior studies, teaches that the lipid removal, or separation, at an early embryo developmental stage is critical for cryopreservation of an IVP (IVF- or NT-derived) porcine embryo, and that besides swelling the zona pellucid through partial enzymatic digestion, the perivitelline space of an IVP porcine embryo may be enlarged by condensing the volume of the embryo to enable easy lipid removal/separation. The invention also discloses that exposing an IVP embryo to a high osmolality treatment may condense the embryo but preserve the vitality of the embryo. Furthermore, the inventive lipid-separation methods may be employed to treat multiple embryos at once, in contrast to the current delipation procedures that require micromanipulation of each individual oocyte or embryo.

Figure 1:
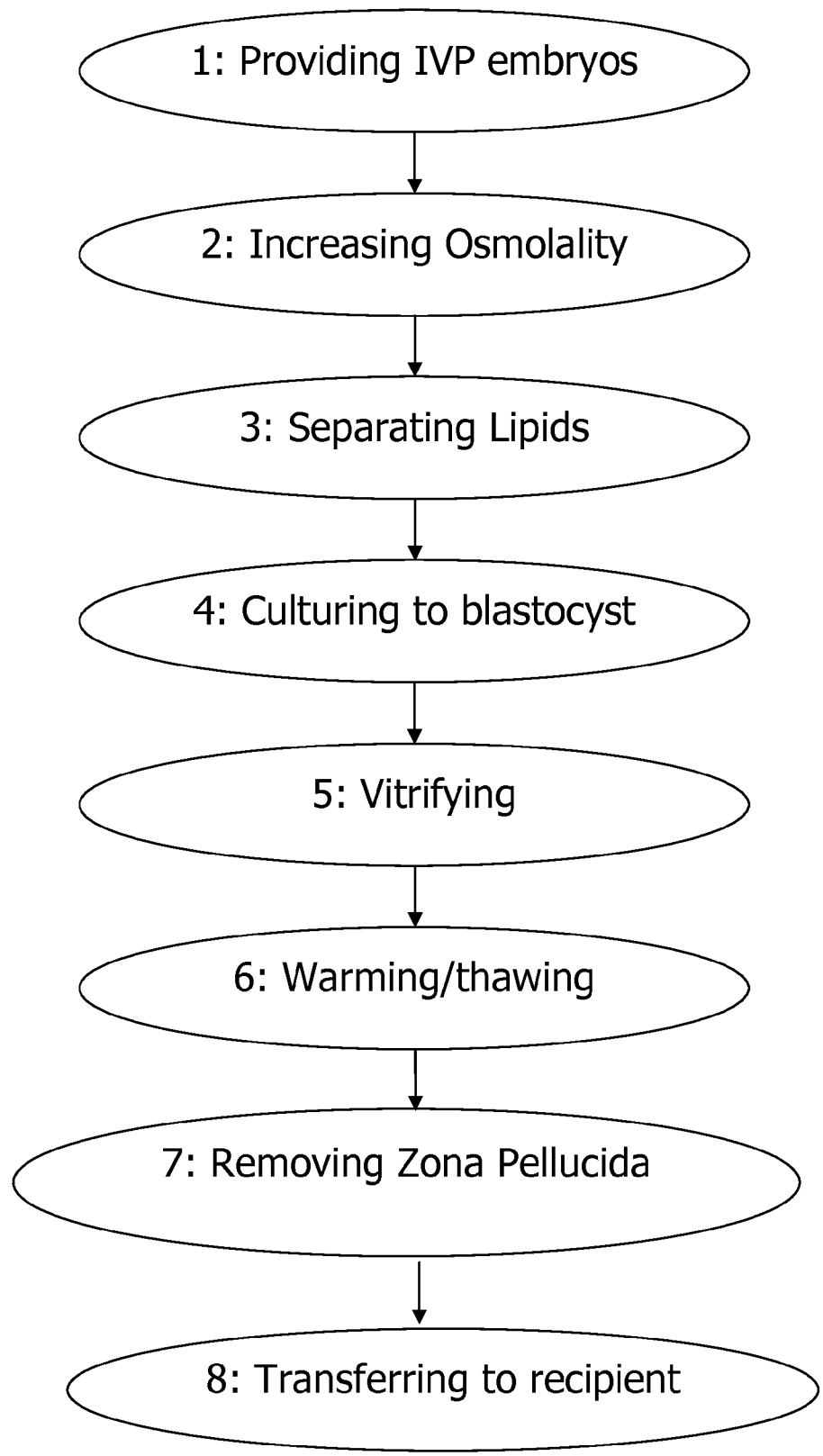
FIG. 1 is a flow diagram of the inventive cryopreservation and recovery process.

Referring to FIG. 1, which is a flow diagram of the inventive cryopreservation and recovery process via the inventive embryo-condensing method. Step 1 in FIG. 1 is to provide IVP embryos at a pre-selected early developmental stage, specifically the one-cell or cleavage stage prior to compaction. Any standard IVP procedure, such as IVF or NT, may be adapted.

According to one embodiment of the inventive method, the in-vitro-fertilization process may start with the oocytes aspirated from the antral follicles of one or multiple pig ovaries. The oocytes may be cultured to maturity in a maturation medium for a period of time and denuded. An exemplary maturation medium may contain TCM 199 (Gibco, 31100035, Grand Island, N.Y.) with 0.1% PVA, 3.05 mmol/L glucose, 0.91 mmol/L sodium pyruvate, 0.57 mmol/L cysteine, 0.5 µg/mL LH, 0.5 µg/mL FSH, 10 ng/mL epidermal growth factor, 75 µg/mL penicillin and 50 µg/mL streptomycin. The oocytes may be cultured in the maturation medium for about 40-44 h at 38.5° C., 5% $CO_2$ in humidified air. After the maturation, the oocytes may be denuded by removing the cumulus cells via vortexing for a short period of time, such as about 4 minutes, in TL-HEPES [20] supplemented with 0.1% PVA and 0.1% hyaluronidase. The denuded oocytes may be stored in many different media before insemination. An excellent medium may contain TCM199 with 0.6 mmol/L $NaHCO_3$, 2.9 mmol/L Hepes, 50 µg/ml penicillin, 60 µg/ml streptomycin, 30 mmol/L NaCl and 3 mg/mL BSA [26].

Any standard insemination procedure may be followed to produce the IVP embryos. According to one embodiment, the denuded oocytes with a polar body may be first transferred to a suitable IVF medium to be combined with a sperm suspension. An exemplary IVF medium may contain a modified Tris-buffered medium with 113.1 mmol/L NaCl, 3 mmol/L KCl, 7.5 mmol/L $CaCl_2$, 5 mmol/L sodium pyruvate, 11 mmol/L glucose, 20 mmol/L Tris, 2 mmol/L caffeine, and 2 mg/mL BSA.

According to another embodiment of the invention, NT-derived embryos may start with nuclear transfer donor cells and commercial oocytes. The nuclear transfer donor cells may be collected from a transgenic piglet or produced through genetic modification of wild type cells. After the oocytes are allowed to mature, the cumulus cells are removed from the oocytes by vortexing for about 4 min in TL-HEPES supplemented with 0.1% PVA and 0.1% hyaluronidase. The first polar body and the adjacent cytoplasm from these oocytes are then aspirated while in manipulation medium with 7.0 µg/ml cytochalasin B. A donor cell is then transferred into the pervitelline space. Fusion and activation can be accomplished simultaneously with two 30 is pulses of 1.2 kV/cm in fusion/sctivation medium (such as 0.3 M mannitol, 1.0 mM $CaCl_2$, 0.1 mM $MgCl_2$, and 0.5 mM HEPES). Alternatively fusion and activation may be accomplished stepwise, first exposing in a fusion only medium with a lower concentration of calcium (such as 0.3 M mannitol, 0.1 mM $CaCl_2$, 0.1 mM $MgCl_2$ and 0.5 mM HEPES), then exposing to 200 µM Thimerosal for about 10 min in the dark and then 8 mM DTT for 30 min to activation [21] or any other suitable method.

After insemination or NT, the IVP embryos are cultured to the one-cell or cleavage stage (zygote, 2-cell or 4-cell stage, prior to compaction). Any suitable culture procedure may be adapted. According to one embodiment, the IVP embryos (derived from in-vitro-fertilization or NT) may be cultured in a variety of different culture media at 38.5° C., 5% $CO_2$ in air for 28 to 30 hours to select 2-cell stage embryos. An exemplary culture medium, PZM3 [27], may contain NaCl 108.0 mmol/L, KCl 10.0 mmol/L, $KH_2PO_4$ 0.35 mmol/L, $MgSO_4.7H_2O$ 0.4 mmol/L, $NaHCO_3$ 25.07 mmol/L, Na-pyruvate 0.2 mmol/L, Ca(Lactate)$_2$.5H2O 2.0 mmol/L, Glutamine 1.0 mmol/L, Hypotaurine 5.0 mmol/L, BME amino acid solution 20 ml/L, MEM amino acid solution 10 ml/L, Gentamicin 0.05 mg/mL, BSA 3 mg/mL, with osmolality at 288±2, and pH at 7.3±2.

Step 2 in FIG. 1 is to increase the osmolality of the embryos to condense the embryo. Several different media formulations may be employed to increase the osmolality in order to condense the volume of an oocyte or embryo. The invention provides examples using NaCl or sucrose at different concentrations (resulting different osmolalities), but other formulations that result in a higher osmolality and subsequent shrinkage of the volume of the cell(s) should work.

According to one embodiment of the inventive method, the osmolality may be increased by adjusting the osmolality of a medium where the embryos are submerged. For example, NaCl or sucrose may be added to a stock medium with about 300 mOsmo (such as a stock solution with 300-310 mOsmo with 7.0 µg/mL cytochalasin B and 0.1 mg/mL BSA) to result a medium with various osmolalities, such as 350, 400, 500, 600 and 800-850 mOsmo. The IVP-derived embryos may be exposed to a pre-selected high osmolality medium for a short period of time, about 5 to 10 min, before centrifugation.

Step 3 in FIG. 1 is to separate the lipid from the condensed embryos, normally through centrifugation. For example, the condensed embryos in the high osmolality medium can be centrifuged at 13,400×g for about 6 to 20 min. The centrifugation condition (force or duration) may likely be varied to a large range of centrifugation force and time as long as it is sufficient to achieve full lipid separation while preserve the vitality of the embryos. A shorter duration may work especially if the force is increased. Likewise a longer duration may be necessary if a lower force is used. Pro-longed exposure to high osmolality may affect the vitality of an embryo.

The lipid separation may be checked after about 12 hours of culturing; in some cases (especially for NT-derived embryos, since they are relatively more valuable) a second round of high osmolality treatment and subsequent centrifugation may be applied to achieve a relatively complete lipid separation. The second high osmolality treatment may be an optional as long as the embryos remain at the cleavage stage prior to compaction.

The lipid-separated embryos are then allowed to develop further to the blastocyst stage Step 4, in FIG. 1. Specifically, the lipid-separated embryos may be cultured in PZM3 for 3 to 6 days for the embryo to attain the blastocyst stage.

Step 5 in FIG. 1 is the vitrification of the further-developed embryos. The embryos may be vitrified via any standard method/procedure. According to one embodiment, the further-developed embryos may be vitrified at the blastocyst stage by using a modified open pulled straw ('OPS') method. Specifically, the further-developed embryos may be placed in an equilibration solution for a short period of time (such as about 2 min) followed by exposure to a vitrification solution, then loaded into an OPS straw and immediately plunged into liquid nitrogen. An exemplary equilibration solution may contain 10% ethylene glycol, 10% dimethyl sulfoxide ('DMSO'), while an exemplary vitrification solution may contain 20% ethylene glycol, and 20% DMSO. The process before plunging into nitrogen may be conducted on a 38.5° C. warm stage. The duration from exposure to the vitrification solution to plunging into nitrogen is generally short ranging between about 25 to 30 seconds.

Steps 6 to 8 in FIG. 1 are steps to recover the preserved embryos and transfer such into a recipient. Specifically, the vitrified embryos may be thawed by immersing into a buffer solution (such as sucrose) for a period of time at a slightly elevated temperature (such as about 38.5 ° C.). The thawed embryos may be treated with 0.5% pronase to soften and remove the zona pellucida. The lipid-separated and zona-removed embryos may then be transferred to the oviduct or uterus of a recipient or surrogate.

FIGS. 2(a)-(f) are the photos of IVF-derived embryos after high osmolality treatment (at 400 mOsm with NaCl). FIG. 2(a) shows the embryos cultured for several hours after high osmolality treatment and centrifugation. FIGS. 2(b) and 2(c) show the embryos at blastocyst stage. FIG. 2(d) shows the embryos after vitrification and warming. FIG. 2(e) shows the embryos after removal of their zona pellucida. FIG. 2(f) shows the re-expanded embryos after in vitro culture in BRL cell conditioned medium.

Figure 3:
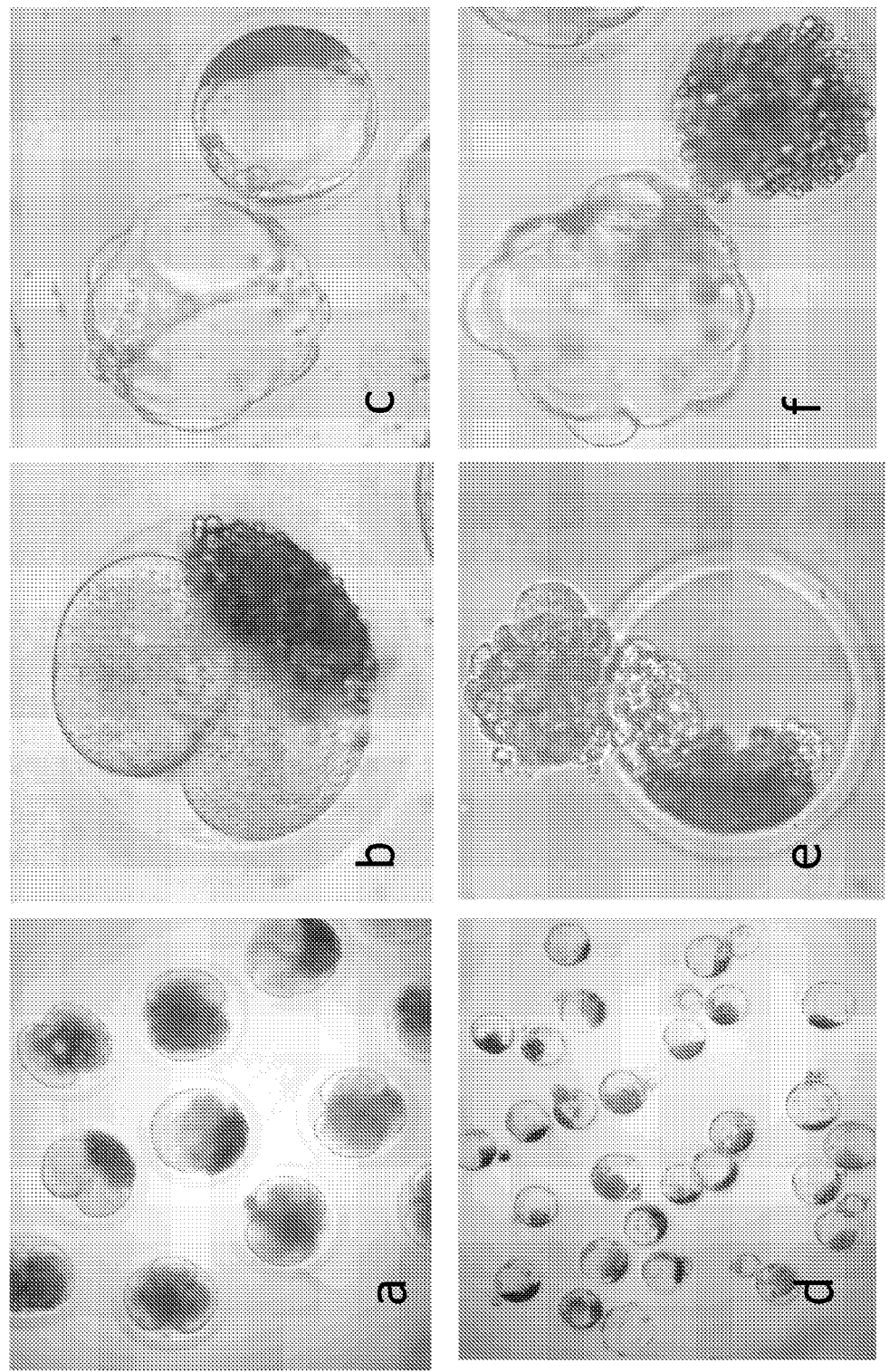
FIGS. 3(a) to (f) are photos of the development of the NT-derived embryos after high osmolality treatment.

FIGS. 3(a)-(f) are the photos of the development of the NT-derived embryos after high osmolality treatment with NaCl or sucrose. FIGS. 3(a) and 3(b) show the NT-derived embryos cultured for several hours after high osmolality treatment and centrifugation; FIGS. 3(c) and 3(d) show the embryos cultured further to the blastocyst stage; FIG. 3(e) shows the embryo warmed after vitrification; and FIG. 3(f) shows the re-expanded embryos after in vitro culture in BRL cell conditional medium.

The invention further studied the effects of different reagents (adjusting osmolality), different osmolality and centrifugation time on the rate of lipid separation. The invention finds that different reagents, such as NaCl or sucrose, have similar effects on lipid separation; the ideal osmolality for lipid separation ranges from about 350 to about 500 mOsm; and centrifugation duration ranging from about 6 minutes to about 20 minutes at a suitable centrifugation force/speed also has a positive effort on the lipid separation rate.

Figure 2:
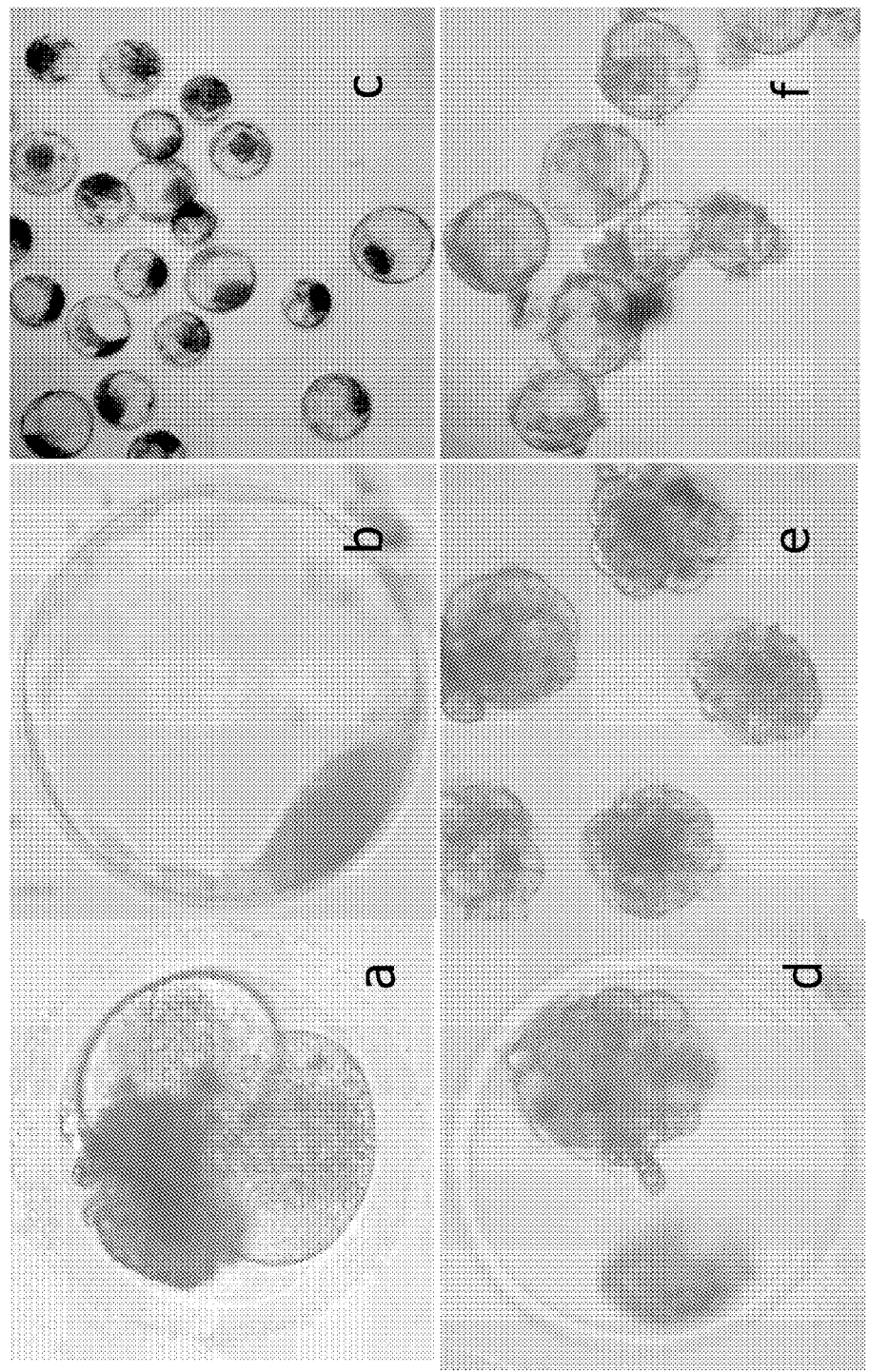
FIGS. 2(a) to (f) are photos of the development of the in-vitro-fertilization derived embryos after high osmolality treatment.
Figure 4:
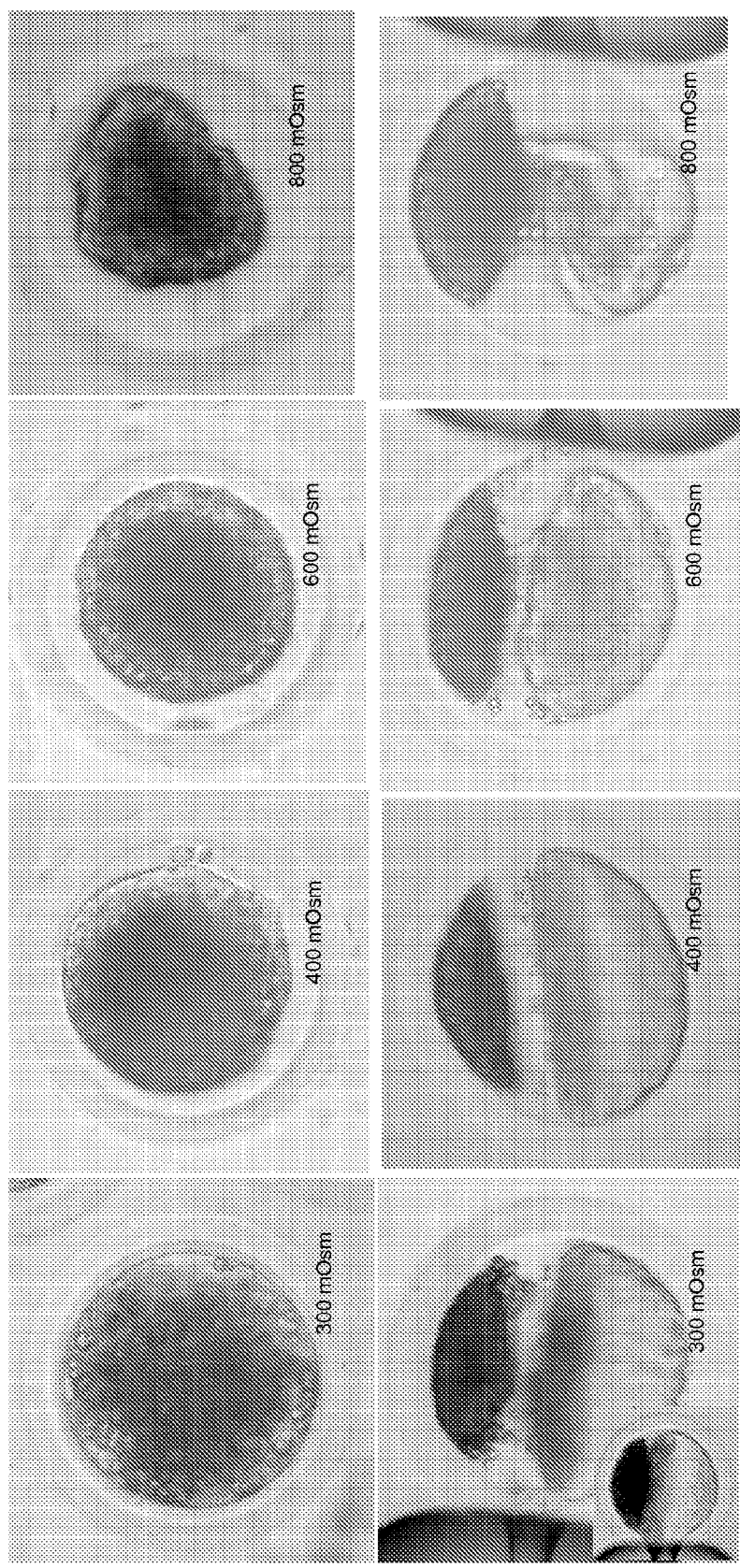
FIG. 4 includes the photos of embryos treated with different osmolalities (adjusted by NaCl or sucrose) (Row 1) and their corresponding photos immediately after centrifugation (Row 2).

FIG. 4 shows the photos of the in-vitro-fertilized embryos treated with different osmolalities (adjusted with NaCl or sucrose) before and after centrifugation. Row 1 shows the photos of embryos exposed at different osmolalities, 300 mOsm (the control), 400 mOsm (adjusted with NaCl), 600 mOsm (adjusted with sucrose), and 800 mOsm (adjusted with sucrose), with condensation clearly shown at the elevated osmolalities (compared to the control). Row 2 lists the corresponding photos of embryos after centrifugation. The bridge-like structure after centrifugation (indicating incomplete lipid separation) can be seen in the control; complete lipid separation can be observed in the embryo exposed at 400 mOsm, while large bridge-like structures are present in the embryos treated with 600 or 800 mOsmo. FIG. 2 indicates that osmolality at about 400 mOsm provides the most complete lipid separation, when osmolality increased to 600 and above, the lipid separation is hindered.

The invention further quantitatively evaluated the impacts of the different osmolalities and centrifugation conditions on the lipid separation rate, the embryos' development, and the hatching ability. Based on the data included in Tables 1 (IVF-derived embryos, osmolality adjusted with NaCl), 2 (IVF-derived embryos, osmalility adjusted with sucrose), and 3 (NT-derived embryos, osmalility adjusted with both NaCl and sucrose, all three tables attached), the preferred condition for lipid separation is to expose the IVP embryos to osmolality ranging from above 300 to about 500 mOsm, preferably from about 350 to about 450 mOsm, followed by centrifugation for about 6 to about 20 minutes at 13,400×g speed. The centrifugation time may be shorten or extended depending upon the centrifugation speed. However, extending centrifugation time may subject the embryos to prolonged exposure to high osmolality, which may have adverse impact on the vitality of the embryos. Furthermore, in Table 3, the second high osmolality treatment is elected for the NT-derived embryos that failed to condense upon the first round of treatment, which increases the total lipid separation rate. The second high osmolality treatment may be elected as long as the embryos are still at the cleavage stage prior to compaction.

TABLE 1

The lipid separation and development of IVP embryos after treatment with different osmolalities and different centrifugation time at 18-20 hrs after the beginning of IVF*

| Treatment | | Total No. of Embryos Treated | Lipid separated embryo | | Development to the blastocyst stage % | | | |
|---|---|---|---|---|---|---|---|---|
| Osmolality | Centrifugation time (min) | | No. | % Mean ± SEM | No. | /Lipid Separated Mean ± SEM | /Total Embryos Mean ± SEM | |
| 300 | 6 | 216 | 106 | 49.1 ± 6.0 $^f$ | 15 | 14.2 ± 5.8 $^{abc}$ | 6.9 ± 3.5 $^{cd}$ |
| 350 |   | 221 | 166 | 75.1 ± 5.3 $^{de}$ | 23 | 13.9 ± 2.3 $^{abc}$ | 10.4 ± 1.6 $^{bcd}$ |
| 400 |   | 217 | 182 | 83.9 ± 4.2 $^{cd}$ | 36 | 19.8 ± 3.7 $^a$ | 16.6 ± 3.2 $^{ab}$ |
| 450 |   | 223 | 200 | 89.7 ± 2.4 $^{ab}$ | 29 | 14.5 ± 3.8 $^{ab}$ | 13.0 ± 3.5 $^{abc}$ |
| 500 |   | 228 | 195 | 85.5 ± 2.2 $^{bc}$ | 35 | 17.9 ± 3.7 $^{ab}$ | 15.4 ± 3.4 $^{ab}$ |
| 300 | 12 | 200 | 133 | 66.5 ± 3.3 $^{de}$ | 24 | 18.4 ± 3.5 $^{ab}$ | 12.0 ± 2.6 $^{abcd}$ |
| 350 |   | 217 | 182 | 83.9 ± 3.0 $^{cd}$ | 33 | 18.1 ± 3.6 $^{ab}$ | 15.2 ± 3.2 $^{ab}$ |
| 400 |   | 216 | 187 | 86.6 ± 3.9 $^{bc}$ | 21 | 11.3 ± 1.8 $^{abc}$ | 9.7 ± 1.5 $^{bcd}$ |
| 450 |   | 213 | 192 | 90.1 ± 3.4 $^{abc}$ | 36 | 18.8 ± 2.8 $^{ab}$ | 16.9 ± 2.9 $^{ab}$ |
| 500 |   | 211 | 200 | 94.8 ± 1.2 $^{ab}$ | 29 | 14.5 ± 2.9 $^{ab}$ | 13.7 ± 2.7 $^{abc}$ |
| 300 | 20 | 216 | 153 | 70.8 ± 5.2 $^{de}$ | 27 | 17.6 ± 5.0 $^{ab}$ | 12.5 ± 3.9 $^{abcd}$ |
| 350 |   | 212 | 193 | 91.0 ± 1.9 $^{abc}$ | 29 | 15.0 ± 2.9 $^{ab}$ | 13.7 ± 2.7 $^{abc}$ |
| 400 |   | 219 | 213 | 97.3 ± 1.6 $^a$ | 27 | 12.7 ± 1.9 $^{abc}$ | 12.3 ± 1.9 $^{abcd}$ |
| 450 |   | 209 | 195 | 93.3 ± 2.2 $^{abc}$ | 21 | 10.8 ± 2.5 $^{bc}$ | 10.0 ± 2.5 $^{bcd}$ |
| 500 |   | 223 | 206 | 92.4 ± 1.5 $^{abc}$ | 12 | 5.8 ± 1.9 $^c$ | 5.4 ± 1.7 $^d$ |
| Control | | 262 | — | — | 47 | 17.9 ± 2.1 $^{ab}$ | 17.9 ± 2.1 $^a$ |

$^{a,b,c,d,e,f}$ Different superscripts within a column are different P < 0.05.
*Summary of six replicates.

TABLE 2

The lipid separation and development of IVP embryos after treatment with different osmolalities and centrifugation for 6 min at 18-20 hrs after IVF*

| Treatment | | Total embryos | Lipid separated embryos | | Development to the blastocyst stage % | | |
|---|---|---|---|---|---|---|---|
| Osmolality | Chemical | | No. | %, lipid separated embryos/Total embryos Mean ± SEM | No. | /Lipid separated embryos Mean ± SEM | /Total embryos Mean ± SEM |
| 400 | NaCl | 133 | 117 | 88.0 ± 9.1 $^a$ | 14 | 12.0 ± 6.1 $^{ab}$ | 10.5 ± 3.5 $^{ab}$ |
| 400 | Sucrose | 92 | 83 | 90.2 ± 0.6 $^{ab}$ | 14 | 16.9 ± 8.1 $^a$ | 15.2 ± 7.2 $^a$ |
| 500 |   | 133 | 97 | 73.0 ± 8.1 $^b$ | 7 | 7.2 ± 1.2 $^{ab}$ | 5.3 ± 0.4 $^{abc}$ |
| 600 |   | 94 | 23 | 24.5 ± 13.0 $^c$ | 1 | 4.3 ± 12.5 $^{ab}$ | 1.1 ± 1.2 $^{bc}$ |
| 800 |   | 125 | 1 | 0.8 ± 0.8 $^c$ | 0 | 0 $^b$ | 0 $^c$ |
| Control | | 144 | — | — | 20 | 3.9 ± 3.4 $^{ab}$ | 13.9 ± 3.4 $^a$ |

*Summary of three replications
$^{a,b,c}$ Different superscripts within a column are different P < 0.05.

TABLE 3

Lipid separation of NT embryos after treatment with different osmolalities and centrifugation times at 14-18 hrs after fusion*

| Treatments | | | | | Lipid separated embryos | | | | Lipid separated blastocysts % (Mean ± SEM) | |
|---|---|---|---|---|---|---|---|---|---|---|
| Osmo | Chemical used to make high osmolality medium | Centrifugation time (min) | Activation and fusion of NT embryos | Total No. of embryos | 1$^{st}$ high osmolality treatment and centrifugation | | 1$^{st}$ + 2$^{nd}$ osmolality treatment and centrifugation | | /Lipid separated embryos | /Total embryos |
| | | | | | No. | % (Mean ± SEM) | No. | % (Mean ± SEM) | No. | |
| 400 | Sucrose | 6 | Low Calcium + Thi + DTT | 531 | 336 | 63.3 ± 2.5 $^d$ | 444 | 83.6 ± 0.9 $^c$ | 73 | 16.4 ± 2.1 $^{ab}$ 13.7 ± 1.6 |

TABLE 3-continued

Lipid separation of NT embryos after treatment with different osmolalities and centrifugation times at 14-18 hrs after fusion*

| Treatments | | | | Lipid separated embryos | | | | Lipid separated blastocysts | |
|---|---|---|---|---|---|---|---|---|---|
| | | | | 1st high osmolality treatment and centrifugation | | 1st + 2nd osmolality treatment and centrifugation | | % (Mean ± SEM) | |
| Osmo | Chemical used to make high osmolality medium | Centrifugation time (min) | Activation and fusion of NT embryos | Total No. of embryos | No. | % (Mean ± SEM) | No. | % (Mean ± SEM) | No. | /Lipid separated embryos | /Total embryos |
| 400 | Sucrose | 6 | Electrical | 818 | 546 | $66.7 \pm 1.7^{bcd}$ | 671 | $82.0 \pm 1.4^{c}$ | 115 | $17.1 \pm 0.8^{ab}$ | $14.1 \pm 0.8$ |
| 400 | NaCl | 6 | Electrical | 109 | 67 | $61.5 \pm 0.4^{cd}$ | 89 | $81.7 \pm 0.2^{c}$ | 22 | $24.7 \pm 2.5^{a}$ | $20.2 \pm 2.0$ |
| 400 | NaCl | 12 | Electrical | 118 | 88 | $74.6 \pm 5.1^{abc}$ | 100 | $84.7 \pm 0.7^{bc}$ | 20 | $20.0 \pm 6.8^{ab}$ | $17.0 \pm 5.7$ |
| 400 | NaCl | 20 | Electrical | 550 | 415 | $75.5 \pm 2.3^{ab}$ | 491 | $89.3 \pm 1.7^{ab}$ | 62 | $12.6 \pm 2.3^{b}$ | $11.3 \pm 2.1$ |
| 350 | NaCl | 20 | Electrical | 712 | 570 | $80.1 \pm 2.9^{a}$ | 653 | $91.7 \pm 0.7^{a}$ | 116 | $17.8 \pm 2.5^{ab}$ | $16.3 \pm 2.4$ |
| | | | Control | 60 | — | — | — | — | 8 | $13.3 \pm 3.3^{b}$ | $13.3 \pm 3.3$ |

*Summary of two to six replicates.
a,b,c,d Different superscripts within a column are different $P < 0.05$.

Table 4 evaluates the pregnancy and offspring data on the IVF-derived embryos preserved by high osmolality treatment, centrifugation and vitrification. Among the data included in Table 4, three surrogates out of nine established pregnancies and produced normal offspring. One surrogate received the embryos treated with osmolality at 350 mOsm and produced five piglets, three males and two females; one surrogate received embryos treated with 400 mOsm and produced four piglets, two males and two females; and one surrogate received the embryos treated with 450 mOsm and produced three piglets, one male and two females.

Table 5 lists the transfer, pregnancy, and offspring data of the NT-derived embryos after high osmolality treatment, centrifugation, and vitrification. Three embryo transfers were performed and recorded. For each transfer, 80 to 90 embryos with the zona pellucida softened or removed by pronase treatment were transferred into the surrogates. Two of the three surrogates receiving the embryos treated with 400 mOsmo with 6 min centrifugation and the one receiving embryos treated with 350 mOsmo with 20 min centrifugation resulted in pregnancy, with the former a single male piglet was produced. The data in Tables 4 and 5 demonstrates that the inventive method, especially when applying the preferred

TABLE 4

Transfer of IVP embryos derived from high osmolality treatment and centrifugation after vitrification and warming.

| Date of ET | Osmo. (mOsm) | Chemical | Centrifuge (min) | Number of embryos transferred | Zona removal after vitrification and warming | Recipient | Pregnancy | No. of Piglets | Note |
|---|---|---|---|---|---|---|---|---|---|
| Jun. 14, 2007 | 350 | NaCl | 6 | 25 | + | O089 | + | 5 | 3 males 2 females |
| Jun. 14, 2007 | 350 | NaCl | 6 | 50 | − | O090 | − | Returned to estrus on day 19 | |
| Jun. 28, 2007 | 350 | NaCl | 6 | 50 | − | O105 | − | Returned to estrus on day 27 | |
| Jul. 5, 2007 | 400 | NaCl | 6 | 25 | + | O082 | − | Returned to estrus on day 21 | |
| Jul. 13, 2007 | 400 | NaCl | 6 | 25 | + | O112 | + | 4 | 2 females 2 males |
| Nov. 1, 2007 | 450 | NaCl | 20 | 25 | + | O174 | − | Returned to estrus on day 25 | |
| Nov. 8, 2007 | 450 | NaCl | 20 | 25 | + | O188 | + | 3 | 2 females 1 male |
| Nov. 9, 2007 | 450 | NaCl | 12 | 25 | + | O128 | − | Returned to estrus on day 24 | |
| Dec. 12, 2007 | 450 | NaCl | 12 | 25 | + | O185 | + | Returned to estrus on day 20 | | range of osmolality (from about 350 to about 450 mOsm), is a successfully cryopreservation method for the IVP embryos.

TABLE 5

Transfer of NT embryos after vitrification and warming *

| Date of embryo transfer | High osmolality treatment | | Number of embryos transferred | Zona removal after vitrification and warming | Recipient | | No. of piglets | Note |
|---|---|---|---|---|---|---|---|---|
| | mOsm | Chemical | Centrifuge (mins) | | No. | Pregnant | | |
| Aug. 24, 2007 | 400 | Sucrose | 6 | 83 | + | O141 | + | 1 (male) | |
| Nov. 16, 2007 | 400 | NaCl | 6-20 | 80 | + | O184 | − | — | Returned on day 22 of the cycle |
| Dec. 6, 2007 | 350 | NaCl | 20 | 90 | + | O214 | + | | Returned on day 19 of the cycle |

* One gilt was not included in the above data as it developed a reproductive tract infection.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

REFERENCES

1. Polge C, Wilmut I, Rowson LEA. The low temperature preservation of cow, sheep, and pig embryos. Cryobiology 1977; 11: 560.
2. Wilmut I. The low temperature preservation of mammalina embryos. Journal of Reproduction and Fertility 1972; 31: 513-514.
3. Dobrinsky J R. Cellular Approach to Cryopreservation of Embryos. Theriogenology 1996; 45: 17-26.
4. Nagashima H, Kashiwazaki N, Ashman R J, Grupen C G, Seamark R F, Nottle M B. Removal of Cytoplasmic Lipid Enhances the Tolerance of Porcine Embryos to Chilling. Biology of Reproduction 1994; 51: 618-622.
5. Dobrinsky J R, Pursel V G, Long C R, Johnson L A. Birth of piglets after transfer of embryos cryopreserved by cytoskeletal stabilization and vitrification. Biology of Reproduction 2000; 62: 564-570.
6. Berthelot F, Martinat-Botte F, Perreau C, Terqui M. Birth of piglets after OPS vitrification and transfer of compacted morula stage embryos with intact zona pellucida. Reproduction, Nutrition, Development 2001; 41: 267-272.
7. Beebe L F S, Cameron R D A, Blackshaw A W, Higgins A, Nottle M B. Piglets born from centrifuged and vitrified early and peri-hatching blastocysts. Theriogenology 2002; 57: 2155-2165.
8. Misumi K, Suzuki M, Sato S, Saito N. Successful production of piglets derived from vitrified morulae and early blastocysts using a microdroplet method. Theriogenology 2003; 60: 253-260.
9. Li R, Lai L, Wax D, Hao Y, Murphy C N, Rieke A, Samuel M, Linville M L, Korte S W, Evans R W, Turk J R, Kang J X, Witt W T, Dai Y, Prather R S. Cloned transgenic swine via in vitro production and cryopreservation. Biology of Reproduction 2006; 75: 226-230.
10. Nagashima H, Hiruma K, Saito H, Tomii R, Ueno S, Nakayama N, Matsunari H, Kurome M. Production of live piglets following cryopreservation of embryos derived from in vitro-matured oocytes. Biology of Reproduction 2007; 76: 900-905.
11. Nagashima H, Cameron R D, Kuwayama M, Young M, Beebe L, Blackshaw A W. Survival of porcine delipated oocytes and embryos after cryopreservation by freezing or vitrification. Journal of Reproduction and Development 1999; 45: 167-176.
12. Cameron R D A, Beebe L F S, Blackshaw A W, Keates H L. Farrowing rates and litter size following transfer of vitrified porcine embryos into a commercial swine herd. Theriogenology 2004; 61: 1533-1543.
13. Esaki R, Ueda H, Kurome M, Hirakawa K, Tomii R, Yoshioka H, Ushijima H, Kuwayama M, Nagashima H. Cryopreservation of porcine embryos derived from in vitro-matured oocytes. Biology of Reproduction 2004; 71: 432-437.
14. Du Y, Zhang Y, Li J, Kragh P M, Kuwayama M, Ieda S, Zhang X, Schmidt M, Bogh I B, Purup S, Pedersen A M, Villemoes K, Yang H, Bolund L, Vajta G. Simplified cryopreservation of porcine cloned blastocysts. Cryobiology 2007; 54: 181-187.
15. Norberg H S. Ultrastructural aspects of the preattached pig embryo: cleavage and early blastocyst stage. Z. Anat. Entwicklungsgesch 1973; 143: 95-114.
16. Kikuchi K, Ekwall H, Tienthai P, Kawai Y, Noguchi J, Kaneko H, Rodriguez-Martinez H. Morphological features of lipid droplet transition during porcine oocyte fertilisation and early embryonic development to blastocyst in vivo and in vitro. Zygote 2002; 10: 355-366.
17. Nagashima H, Kato Y, Yamakawa H, Matsumoto T, Ogwa S. Changes in freezing tolerance of pig blastocysts in perihatching stages. Jpn J Animal Reproduction 1989; 35: 130-134.
18. Nagashima H, Yamakawa H, Niemann H. Freezability of porcine blastocysts at different peri-hatching stages. Theriogenology 1992; 37: 839-850.
19. Li R, Hosoe M, Shioya Y, Bou S. The preliminary research on freezing viability of bovine in vitro fertilized embryos. Chinese J Scientia Agricultura Sinica 2002; 35: 1125-1129.
20. Tao T, Machaty Z, Boquest A C, Day B N, Prather R S. Development of pig embryos reconstructed by microinjection of cultured fetal fibroblast cells into in vitro matured oocytes. Animal Reproduction Science 1999; 56: 133-141.

21. Machaty Z, Wang W H, Day B N, Prather R S. Complete Activation of Porcine Oocytes Induced by the Sulfhydryl Reagent, Thimerosal. Biology of Reproduction 1997; 57: 1123-1127.
22. Niemann H, Rath D, Wrenzycki C. Advances in biotechnology: New tools in future pig production for agriculture and biomedicine [Review]. Reproduction in Domestic Animals 2003; 38: 82-89.
23. Prather R S, Hawley R J, Carter D B, Lai L, Greenstein J L. Transgenic swine for biomedicine and agriculture. Theriogenology 2003; 59: 115-123.
24. Lai L X, Kolber-Simonds D, Park K W, Cheong H T, Greenstein J L, Im G S, Samuel M, Bonk A, Rieke A, Day B N, Murphy C N, Carter D B, Hawley R J, Prather R S. Production of alpha-1,3-galactosyltransferase knockout pigs by nuclear transfer coning. Science 2002; 295: 1089-1092.
25. Du Y, Kragh P M, Zhang X, Pump S, Yang H, Bolund L, Vajta G. High overall efficiency of porcine handmade cloning (HMC) combining partial zona digestion and oocyte trisection with sequential culture. Cloning and Stem Cells 2005; 7: 199-205.
26. Kragh P M, Du Y, Corydon T J, Pump S, Bolund L, Vajta G. Efficient in vitro production of porcine blastocysts by handmade cloning with a combined electrical and chemical activation. Theriogenology 2005; 64: 1536-1545.
27. Collins J L, Baltz J M. Estimates of mouse oviductal fluid tonicity based on osmotic responses of embryos. Biology of Reproduction 1999; 60: 1188-1193.
28. Li R F, Whitworth K, Lai L X, Wax D, Spate L, Murphy C N, Rieke A, Isom C, Hao Y H, Zhong Z S, Katayama M, Schatten H, Prather R S. Concentration and composition of free amino acids and osmolalities of porcine oviductal and uterine fluid and their effects on development of porcine IVF embryos. Molecular Reproduction & Development 2007; 74: 1228-1235.
29. Hwang I-S, Park M-R, Moon H-J, Shim J-H, Kim D-H, Yang B-C, Ko Y-G, Yang B-S, Cheong H T, Im G S. Osmolarity at early culture stage affects development and expression of apoptosis related genes (Bax-a and Bcl-xl) in pre-Oimplantation porcine NT embryos. Molecular Reproduction & Development 2008; 75: 464-471.
30. Dobrinsky J R. Advancements in cryopreservation of domestic animal embryos. Theriogenology 57(1 Special Issue 2002; 57: 285-302.
31. Beebe L F S, Cameron R D A, Blackshaw A W, Keates H L, Nottle M B. Assisted hatching improves post-warming in vitro viability of vitrified porcine embryos. Reproduction, Fertility & Development 2004; 16: 164.

What is claimed is:

1. A method for delipation of an in vitro produced porcine embryo comprising:
   incubating an in vitro produced porcine embryo in a medium having an osmolality of 350 mOsm to 600 mOsm to produce a condensed embryo; and
   centrifuging the condensed embryo to separate lipids from cytoplasm to produce a lipid-separated embryo.

2. The method of claim 1, further comprising cryopreserving the in vitro produced porcine embryo, wherein said preserving comprises:
   culturing the lipid-separated embryo to the blastocyst stage to produce a lipid-separated blastocyst; and
   cryopreserving the blastocyst by vitrification or freezing to produce a cryopreserved embryo.

3. The method of claim 2 further comprising recovery and transfer of the cryopreserved embryo into a recipient, wherein said recovery and transfer comprise:
   warming and rehydrating the cryopreserved embryo;
   removing the zona pellucida from the embryo; and
   transferring the embryo into a recipient.

4. The method of claim 1, wherein the medium has an osmolality of 350 mOsm to 500 mOsm, or 350 mOsm to 450 mOsm.

5. The method of claim 1, wherein the medium has an osmolality of 350 mOsm, 400 mOsm, or 500 mOsm.

6. The method of claim 1, wherein the osmolality of the medium is adjusted by the addition of a salt, a sugar, or an organic reagent to produce the medium having an osmolality.

7. The method of claim 6, wherein the salt is sodium chloride; wherein the sugar is sucrose, raffinose, fructose, mannitol, or trehalose; or wherein the organic reagent is dimethyl sulfoxide (DMSO) or ethylene glycol.

8. The method of claim 7 wherein the osmolality of the medium is adjusted by the addition of sodium chloride or sucrose to produce the medium having an osmolality, the osmolality being 350 mOsm, 400 mOsm, or 500 mOsm.

9. The method of claim 8, wherein the medium is adjusted by the addition of sodium chloride or sucrose to produce the medium having an osmolality, the osmolality being 400 mOsm.

10. The method of claim 1, wherein the embryo is produced by in vitro fertilization or nuclear transfer.

11. The method of claim 1, wherein the embryo to be incubated in the medium is at the one cell or cleavage stage, prior to compaction.

12. The method of claim 1 wherein the embryo is incubated in the medium for a period of 5 to 10 minutes and wherein the embryo is centrifuged at 13,400×g for 6 to 20 minutes.

13. The method claim 1 wherein multiple embryos are delipated at the same time.

14. A method for delipation, cryopreservation, and recovery of an in vitro produced porcine embryo comprising:
   incubating an in vitro produced porcine embryo in a medium having an osmolality of 350 mOsm to 600 mOsm to produce a condensed embryo;
   centrifuging the condensed embryo to separate lipids from cytoplasm to produce a lipid-separated embryo;
   culturing the lipid-separated embryo to the blastocyst stage to produce a lipid-separated blastocyst;
   cryopreserving the blastocyst by vitrification or freezing to produce a cryopreserved embryo;
   warming and rehydrating the cryopreserved embryo;
   removing the zona pellucida from the embryo; and
   transferring the embryo into a recipient.

15. The method of claim 14, wherein the medium has an osmolality of 350 mOsm to 500 mOsm, or 350 mOsm to 450 mOsm.

16. The method of claim 14, wherein the medium has an osmolality of 350 mOsm, 400 mOsm, or 500 mOsm.

17. The method of claim 14, wherein the osmolality of the medium is adjusted by the addition of a salt, a sugar, or an organic reagent.

18. The method of claim 17, wherein the salt is sodium chloride; wherein the sugar is sucrose, raffinose, fructose, mannitol, or trehalose; or wherein the organic reagent is dimethyl sulfoxide (DMSO) or ethylene glycol.

19. The method of claim 14, wherein the embryo to be incubated in the medium is at the one cell or cleavage stage, prior to compaction.

20. The method claim 14 wherein multiple embryos are delipated at the same time.

* * * * *